United States Patent [19]

Uthoff

[11] Patent Number: 5,102,332
[45] Date of Patent: Apr. 7, 1992

[54] BRAIDED FIBER DENTAL RETAINER AND CONTAINER THEREFOR

[75] Inventor: David C. Uthoff, Belgrade, Mont.

[73] Assignee: Ticore Dental Systems, Bozeman, Mont.

[21] Appl. No.: 660,720

[22] Filed: Feb. 25, 1991

[51] Int. Cl.⁵ ............................................. A61C 3/00
[52] U.S. Cl. .................................... 433/6; 433/215; 206/63.5
[58] Field of Search ............... 433/215, 229, 180, 6, 433/9; 206/63.3, 63.5, 69, 368, 369

[56] References Cited

U.S. PATENT DOCUMENTS

| | | | |
|---|---|---|---|
| 3,378,925 | 4/1968 | Faller | 206/63.5 |
| 4,386,908 | 6/1983 | Kurz | 433/9 |
| 4,504,229 | 3/1985 | Garito et al. | 433/215 |
| 4,516,938 | 5/1985 | Hall | 433/215 |
| 4,533,320 | 8/1985 | Piekarsky | 433/9 |
| 4,609,350 | 9/1986 | Krause | 433/9 |
| 4,669,981 | 6/1987 | Kurz | 433/9 |
| 4,735,571 | 4/1988 | Salvo | 433/215 |

OTHER PUBLICATIONS

The Jun. 1989 *JCO* advertisement by OREC Corporation, vol. XXIII, No. 6.

*Primary Examiner*—Cary E. O'Connor
*Attorney, Agent, or Firm*—Loren H. Uthoff, Jr.

[57] ABSTRACT

A container for a dental retainer consisting of a straight or curved section of hollow tubular material that is opaque to a resin curing light source which encloses a length of fiber which can be braided that is preimpregnated with a light curable bonding resin where two end caps seal the ends of the container one of which is removed upon application of the retainer material which is slowly withdrawn as needed from the container and bonded by light curing the resin to each tooth in sequence. Using the container and the braided fiber, the retainer is easier to align, bond and trim to the teeth producing a more functional and cosmetically pleasing result.

11 Claims, 3 Drawing Sheets

BRAIDED FIBER DENTAL RETAINER AND CONTAINER THEREFOR

FIELD OF THE INVENTION

This invention relates to dental appliances and more specifically to retainer devices and discloses a container for the handling and installation of a retainer made from braided fibers which have been pre-impregnated with light curable bonding resin for bonding to a plurality of teeth using the container to aid in the installation process thereby resulting in a more aesthetically pleasing and functional result.

BACKGROUND OF THE INVENTION

This invention relates in general to a dental bondable retainer for use in the dental treatment of patients and more particularly to a retainer made of a braided fibrous material which has been pre-impregnated with a light curable bonding resin which is transported in an opaque container prior to and during installation.

Heretofore, it has been well known to fabricate preformed or custommade bondable retainers from round or rectangular solid or twisted wire and to bond the wire to adjacent teeth using methods described in the prior art such as that described in U.S. Pat. No. 4,516,938 and incorporated herein by reference. Further, it has been known to use a twisted fibrous material as a dental retainer which is bonded to adjacent teeth using a bonding cement such as a polymerizable resin as described in U.S. Pat. No. 4,504,229 and incorporated herein by reference.

Many problems have been encountered with the use of bondable fibrous retainers in the processes of handling, trimming, resin coating, placement on the teeth and bonding. Heretofore, the dental practitioner has prepared a length of twisted fibers by first trimming to length by cutting to fit the dental arch length in need of retention. The cutting process often results in untwisting and fraying of the twisted fibers. These fibers are then coated with a commercially available light curable bonding resin which results in a further degradation of the retainer quality by increased untwisting and fraying. The teeth are prepared for bonding of the retainer with an acid etching process which is well known in the art.

Placement of the resin coated fiber retainer on the inside of the patient's teeth and subsequent bonding of the fiber to each individual tooth is difficult while maintaining the already diminished integrity of the twisted fiber.

Another problem is encountered in the process of bonding the retainer to each individual tooth in sequence. Since the retainer has been coated with the light curable bonding resin over its complete length, the curing light source bleeds over and causes the resin to be cured in undesired areas. Ideally, only that resin involved in the bonding to a single tooth should be cured. Premature curing of adjacent areas serves to increase the difficulty of the installation process and the final result is often less precise than that which could have been attained if the resin hardening was confined to a specific area.

Known in the art and available to dental practitioners in the commercial marketplace is a fiber retainer made out of Kevlar ® and sold by OREC ® Corporation. Said retainer fiber is a longitudinally oriented twisted thread that tends to untwist and fray when cut or coated with bonding resin making handling and installation difficult with a less than desired result. Also, the yellow color of the Kevlar ® material does not blend with the color of the teeth making for a noticeable retainer which is undesirable from the patient's perspective.

Overall, due to these problems, the installation of the retainer is difficult, the resulting function is impaired, and the final result is aesthetically less than desirable. As will become apparent from the following disclosure, the devices and processes for retention of teeth described herein overcome these difficulties resulting in an improved dental result.

SUMMARY OF THE INVENTION

An object of the present invention is to provide a container for the transportation, handling and installation of a dental retainer which has been coated or pre-impregnated with a light curable bonding resin with greater ease and an improved result.

Briefly stated, in accordance with one aspect of the invention, the fiber retainer which has been pre-impregnated with bonding resin is placed in a hollow, tubular, opaque container that is sealed with two end caps or by other sealing means such as crimping, heat fusing or plugging. When ready for installation, the container is unsealed and then placed on the backside of the teeth. Just enough of the fiber retainer is withdrawn from the container for bonding to each tooth in sequence by light curing of the bonding resin. The container functions to block the light source to prevent unwanted resin curing. Depending on the specific case, the container can be a straight section or curved to best fit the patient's dental arch.

Another object of the present invention is to provide an improved fiber configuration for a dental retainer that facilitates trimming, handling and installation by reducing untwisting, fraying and unravelling.

As opposed to the current practice of loose twisting, the fiberous retainer material disclosed herein is braided using any commercially acceptable braiding pattern. Braiding serves to limit the untwisting, fraying and unravelling of the retainer as it is handled, cut, coated with resin, installed and trimmed after installation. A braided fiber retainer made from a commercial fiber such as Spectra ® overcomes the undesirable characteristics of the prior art by providing resistance to untwisting fraying and unraveling and its color more nearly matches the color of the teeth thereby producing a more aesthetically pleasing result. Also, Spectra's ® low melting temperature facilitates easy trimming with a dental bur due to the heating of the fiber by friction against the bur which causes localized melting and results in a clean trimming cut.

In accordance with another aspect of the invention, the manufacture of the container with the resin coated fiber retainer therein is facilitated by making a long length of the tubular container material and then inserting a like length of fiber or other retainer material which has been coated with a bonding material prior to or after insertion. The long length of the container material with the inserted retainer is then cut into sections and the open ends are sealed thereby completing the retainer assembly.

BRIEF DESCRIPTION OF THE DRAWINGS

Other objects, features and advantages of the invention will be apparent from the following detailed disclosure, taken in conjunction with the accompanying sheets of drawing figures, wherein like reference numerals refer to like parts in which.

DETAILED DESCRIPTION OF THE PREFERRED EMBODIMENT

Hereinafter, embodiments of the present invention will be described with reference to the drawings.

Figure 1:
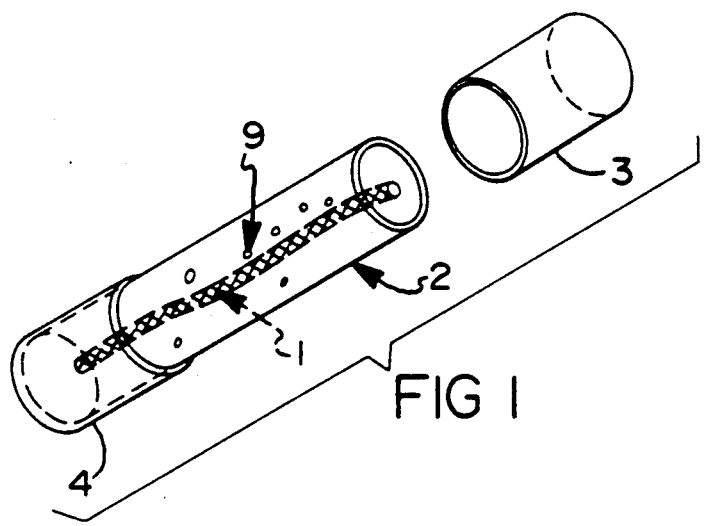
FIG. 1 is a side view showing the container with end caps, one of which is open showing the resin coated fiber material.

FIG. 1 shows a dental retainer package consisting of a tubular shaped container 2 with end caps 3 and 4 which holds a dental retainer 1 which consists of a length of fiberous material which has been pre-impregnated with a light curable bonding resin and will function as a retainer when bonded to a series of teeth. Although the retainer 1 can be made out of a length of steel cable or a single steel wire, the bondable retainer 1 of the invention is preferably made from a plurality of high strength man-made fibers such as those known commercially as Kevlar ® or Spectra ®. Heretofore, the fibers have been loosely twisted to form a larger diameter cross-section with increased strength but with a tendency to untwist, unravel or fray. As described herein, braiding the fibers serves to limit the tendency to untwist, unravel or fray especially when impregnating or cutting the retainer to the proper length.

The container 2 is preferably tubular and preferably made of a plastic material that is impervious to the bonding resin and chemicals found in a patient's mouth. Also, the container 2 is opaque to the light source used to cure the bonding resin. The container 2 serves to hold the dental retainer 1 and the light curable bonding resin 9 which can be used to pre-impregnate the retainer 1 fiber or injected into the container 2 either prior to insertion of retainer 1 or subsequently.

End caps 3 and 4 are used to seal the two open ends of the tubular container 2. They can be but are not necessarily opaque to a resin curing light source. Prior to installation of the retainer 1, one end cap 3 is removed to allow the withdrawal of a short length of the retainer 1 for bonding to the first tooth.

Figure 2:
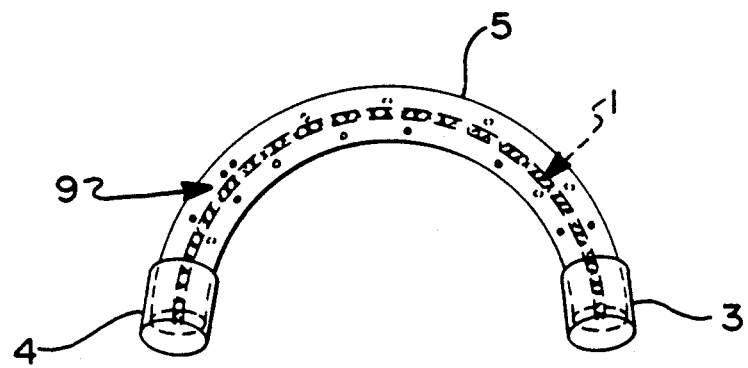
FIG. 2 is similar to FIG. 1 but shows a container curved so as to approximate that of a dental arch.

FIG. 2 shows a container 5 similar to container 2 but has been curved so as to approximate the curvature of a typical dental arch so as to facilitate placement in the patient's mouth on the teeth to be stabilized with the retainer 1. Said containers 2 or 5 can be made of a flexible material so as to allow for easier placement in the mouth.

Figure 3:
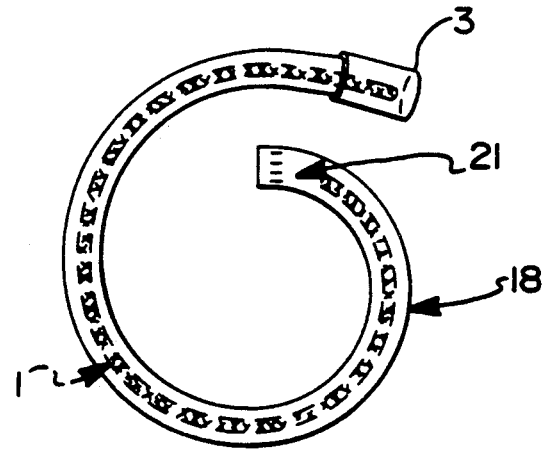
FIG. 3 is similar to FIG. 2 but shows a container with a smaller radius of curvature.

FIG. 3 shows such a container 18 which has been curved to a greater extent than that shown in FIG. 2 so that the curvature exceeds that needed to match the patient's dental arch. By tightly curving the container 18, a longer retainer 1 can be installed with greater ease. The ends can be sealed by a variety of means some of which are described herein. Again, the container 18 can be fabricated from a flexible material thereby easing installation by more easily conforming to the dental arch. One end 21 of said container 18 has been crimped for sealing as opposed to the use of cap 3.

Figure 4:
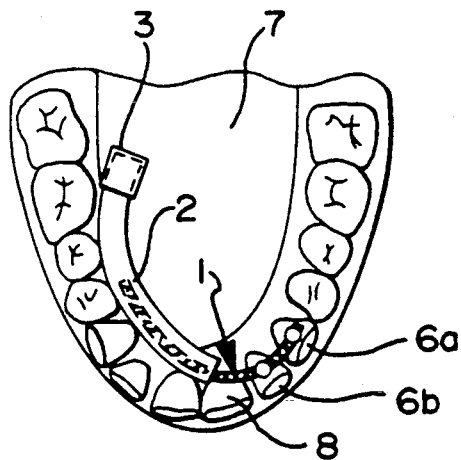
FIG. 4 is a top view of a lower arch having one form of the fiberous dental retainer partially installed.

FIG. 4 shows a container 2 with one end cap 3 removed and a short section of fiber retainer 1 withdrawn and placed in the dental arch 7 of a patient. By only withdrawing that section of the retainer 1 required for bonding, the opaque nature of the containers 2, 5 or 18 prevents resin curing of the retainer in inappropriate sections not immediately involved in the bonding process. The fiber retainer 1 has been bonded to two teeth 6a and 6b sequentially and tooth 8 is ready for bonding by withdrawing just enough of the fiber 1 from the container 2 to bond the tooth 8. In the bonding process, the fiber retainer 1 is held against a tooth that has been prepared by acid-etching and the resin is then cured by using a light source. After bonding to all of the teeth required for retention and stabilization in a like manner, the excess fiber is trimmed preferably with the use of a dental bur so that the ends of the fibers are melted and fused for a clean trimming cut.

Figure 5:
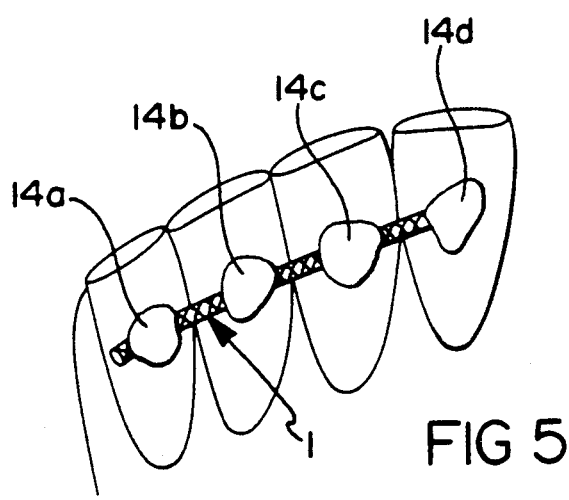
FIG. 5 is similar to FIG. 4 but shows the dental retainer fully installed with resin bonding to adjacent teeth for stabilization.

FIG. 5 shows a fiber retainer 1 installed with resin bonding to a series of teeth 14a, 14b, 14c, 14d thereby providing positioning and stabilization. The container 2 has been removed and the fiber retainer 1 has been trimmed to the proper length. This shows the final result of the installation process. If the length of the retainer 1 is insufficient, another retainer can be positioned to overlap the first and the bonding can be continued to the remaining teeth.

Figure 6:
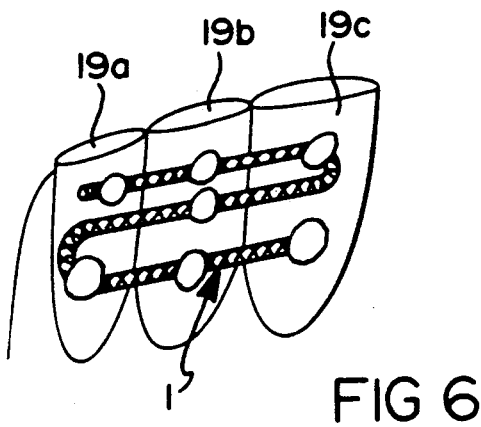
FIG. 6 shows a series of teeth that have been stabilized with a retainer that has been reversed and bonded to increase strength.

If additional strength is needed for retention of teeth, the retainer fiber 1 can be bonded to all of the required teeth, then fiber 1 can be reversed in direction and bonded to the same teeth but in the reverse sequence, and this can be repeated a number of times. FIG. 6 shows a series of teeth 19a, 19b, 19c that have been stabilized with a plurality of retainer 1 runs across the same teeth for increased strength.

Figure 7:
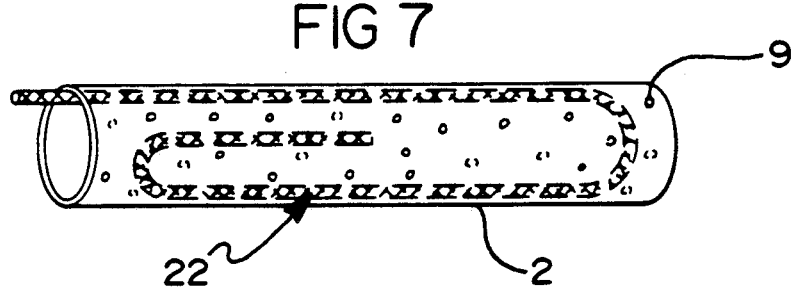
FIG. 7 is similar to FIG. 1 but shows a fiber whose length exceeds that of the container packed into said container.

FIG. 7 shows how a long fiber retainer 22 can be packed into a standard container 2 by allowing the excess to fold or coil within the container 2. Said fiber retainer 22 is pre-impregnated or covered with resin 9 prior to insertion into the container 2.

For high volume manufacture of the container 2 and dental retainer 1, a long section of retainer 1 is impregnated with resin and then inserted into a long section of container 2 material. In the alternative, the bonding resin can be injected at a later time or can be used to pre-impregnate the retainer 1 concurrent with its insertion into the container 2. Sections of the desired length of container 2 are then cut off of the long length of material. The end caps 3 and 4 are then installed on each section or the ends are sealed by crimping 15a, 15b, heat fusing or plugging 16 as described herein thereby completing the assembly.

Figure 8:
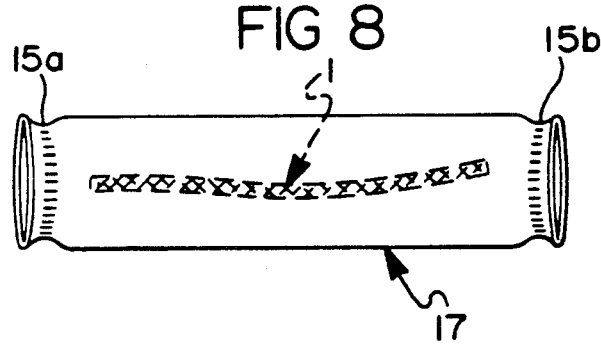
FIG. 8 shows a container that has been sealed by crimping and heat fusion.

FIG. 8 shows a container 17 which has been sealed by crimping only or by crimping and localized heating of the crimped areas 15a, 15b so as to fuse the plastic material. The use of heat and pressure to seal plastic tubing is well known in the art. This sealing process is an alternative to the end caps 3, 4 or by a plug 16.

Figure 9:
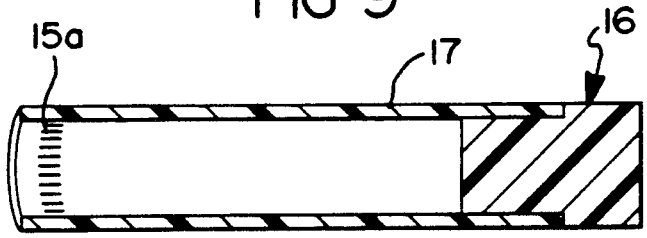
FIG. 9 shows a container that has been sealed by plugging.

FIG. 9 shows a plug 16 inserted into the tubular container 2 so as to seal that end from loss of resin or intrusion of contaminants. The plug 16 where it engages the container 2 is slightly larger in diameter than the inside diameter of the container 2 so that it is retained in position by friction.

Figure 10:
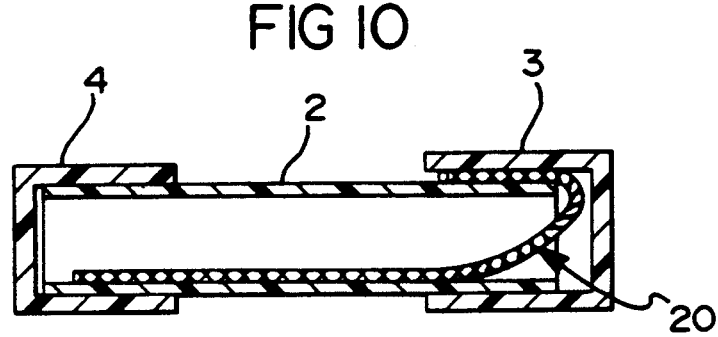
FIG. 10 shows a container with end caps where the resin coated fiber material is extended beyond the end of the container and folded back under the end cap.

FIG. 10 shows a container 2 enclosing a length of fiber retainer 20 which extends past the end of said container 2 and is folded back along the outside surface of said container 2 and is trapped in place by the end cap 3. In this manner, it is easier for the dental practitioner to extract the fiber retainer 1 when installing said retainer 1 by withdrawing the required length of grasping the excess length 20 that has been folded over the end of said container 2.

The fiber dental retainer is installed in the patient's mouth as follows:

One of the two container end caps 3,4 is removed or an end opened by cutting or unplugging thereby exposing said fiber retainer 1 which is pre-impregnated with bonding resin. Several light curable bonding resins are available from commercial suppliers available to dental practitioners in the form of viscous pastes, liquids or creams which will harden usually by polymerization. Said fiber retainer 1 is slowly withdrawn from said container 2 so as to make only enough fiber accessible to cover one tooth. Said container and withdrawn fiber is placed inside the patient's mouth and positioned so that said withdrawn fiber 1 is against one of the teeth to be retained which has been prepared for bonding by acid etching which is well known in the art. Said fiber retainer 1 is then bonded to said tooth by exposing the resin to a curing light source. Said fiber retainer 1 is then further withdrawn from the container to cover another tooth to be retained. Said fiber retainer 1 is then bonded to the second tooth using the curing light source. The balance of the teeth that require retention are bonded to a section of said withdrawn fiber retainer 1 in a similar fashion. Additional bonding resin can be added to each tooth and cured to increase the strength of the retainer bond as required. Upon completion, the excess fiber retainer 1 is trimmed to length and if a low melting temperature fiber is used such as Spectra ®, the end can be melted with a dental bur to make for a clean trimmed end.

In accordance with the present invention, the transport, handling, trimming and particularly installation bonding of a dental retainer 1 has been facilitated with the use of a straight or curved length of an opaque tubular container 2, 5, 18 in which a length of braided fiberous material 1 which has been pre-impregnated with light curable bonding resin 9 has been inserted therein and the container has been sealed for handling and is opened just prior to installation.

What is claimed is:

1. A dental retainer package comprising:
   a container made of a tubular material that is opaque to a bonding resin curing light source;
   a means for sealing ends of said container; and
   a dental retainer made of a plurality of fibers confined within said container where said fibers are intertwined to form a string and said string is coated with a light curable bonding resin whereby said string functions as a dental retainer when removed from said container and bonded to a plurality of teeth.

2. The dental retainer package according to claim 1, wherein a short length of said string extends beyond the end of said container and is held in position by said sealing means.

3. The dental retainer package according to claim 1, wherein said container is curved so as to approximate the shape of a dental arch.

4. The dental retainer package according to claim 1, wherein said fibers are braided to form said string.

5. The dental retainer package according to claim 1, wherein said container is sealed by at least one end cap which is pressed onto the open end of said container.

6. The dental retainer package according to claim 1, wherein said container is sealed by crimping and heating.

7. The dental retainer package according to claim 1, wherein said container is sealed by at least one plug pressed into the open end of said container.

8. The dental retainer package of claim 1, wherein said container is made of a flexible material that can be easily deflected so as to conform to a lingual arch.

9. A dental retainer comprising a plurality of fibers that are braided to form a string that is coated with a light curable bonding resin.

10. A method of manufacturing a dental retainer package, which comprises:
   (a) impregnating a fiber string with a light curable bonding resin;
   (b) feeding said string into and through a length of tube;
   (c) then cutting said tube perpendicular to its length into sections; and
   (d) then sealing the ends of said tube thereby completing said dental retainer package.

11. A method of installing a dental retainer, which comprises:
   placing said dental retainer into a container; coating said retainer with a light curable bonding resin; then placing said container with said dental retainer therein into a patient's dental arch region; withdrawing a length of said retainer only sufficient for bonding to one tooth; bonding said retainer to said tooth by exposing said bonding resin to a curing light source; then withdrawing another length of said retainer sufficient for bonding to a second tooth; and continuing in a like manner until all of the teeth to be stabilized have been bonded to said retainer.

* * * * *